United States Patent [19]

Reichwein

[11] Patent Number: 5,008,906
[45] Date of Patent: Apr. 16, 1991

[54] CONSISTENCY MEASURING DEVICE FOR A SLURRY CONTAINING DEFOAMER

[75] Inventor: David P. Reichwein, Hershey, Pa.

[73] Assignee: Armstrong World Industries, Inc., Lancaster, Pa.

[21] Appl. No.: 404,620

[22] Filed: Sep. 8, 1989

Related U.S. Application Data

[63] Continuation-in-part of Ser. No. 252,067, Oct. 3, 1988, abandoned.

[51] Int. Cl.$^5$ ............................................. G01N 23/14
[52] U.S. Cl. ..................................... 378/54; 250/435; 378/51
[58] Field of Search .......................... 250/390.06, 435; 378/54, 55, 56, 51; 162/258, 263

[56] References Cited

U.S. PATENT DOCUMENTS

| | | | |
|---|---|---|---|
| 2,534,352 | 12/1950 | Herzog | 250/375 |
| 3,060,313 | 10/1962 | Ohmart et al. | 378/56 |
| 3,787,683 | 1/1974 | Kishel | 378/54 |
| 4,024,400 | 5/1977 | Blytas et al. | 378/53 |
| 4,414,472 | 11/1983 | Watt | 250/390.06 |

Primary Examiner—Carolyn E. Fields

[57] ABSTRACT

An on-line method for consistency (percent solids by weight) testing of slurries. An aqueous slurry is deaerated and subjected to a nuclear density (gamma radiation) gauge which is oriented to irradiate the slurry along the axis of a pipe section. Pipe elbows at the ends of the test pipe section permit simple attachment of the nuclear density gauge so that the axially-aligned radiation can be used with various pipe lengths. The electrical output of the gauge is read to immediately furnish a real time reading of consistency.

3 Claims, 1 Drawing Sheet

CONSISTENCY MEASURING DEVICE FOR A SLURRY CONTAINING DEFOAMER

CROSS-REFERRENCE TO RELATED APPLICATION

This application is a continuation-in-part of U.S. application Ser. No. 252,067, filed Oct. 3, 1988, now abandoned, entitled "Consistency Measuring Device for a Slurry".

SUMMARY OF THE INVENTION

This invention deals generally with testing of a liquid suspension of solids and more specifically with the consistency testing of slurries.

Virtually all methods of testing the consistency, the percent of solids in slurries, which are liquid solutions with insoluble solids suspended in them, involve either sampling, gamma radiation or ultrasonic transmission. Sampling is, of course, by its nature an intermittent process which is generally unsatisfactory for high volume production processes which can change between samples.

Ultrasonic testing also has its limitations in the range of values it can measure. These limitations are particularly evident in aqueous solutions where the dry weight of solids surpasses three percent.

With one of the more advanced density measurements, a nuclear density gauge is used to evaluate the quantity of solid material in the slurry. This device measures the attenuation of gamma radiation transmission through the slurry and thereby accurately evaluates the total density of solids and liquid in the slurry.

Both the prior art ultrasonic and nuclear density gauge involve essentially the same test configuration. A transmitter, which in the case of the nuclear density gauge is a gamma radiation source, is attached to the outside circumference of a pipe through which is pumped the slurry to be tested. A detector is then attached to a point on the outside of the pipe which is diametrically opposite the gamma source, and the parameter read is the intensity of the radiation which is detected by the radiation detector. The radiation detected varies with the consistency of the slurry because the solids in the slurry absorb and attenuate the radiation passing through the diameter of the pipe, and as the percentages of solids in the slurry increases, the radiation reaching the detector decreases.

The attenuation of radiation is also affected by the pipe diameter. Clearly, as the diameter of the test pipe is increased, the path length of the radiation is also increased and the attenuation of the radiation increases for any particular slurry consistency. The diameter of the containment pipe therefore affects the sensitivity and accuracy of the test since longer paths provide higher attenuation and make it easier to distinguish small changes within the range of attenuation measured.

This logic has tended to increase the diameter of pipe used in test stations, and that not only increases the cost and size of the installation, but it also has practical limits. It is simply impractical to use large diameter pipes which are greatly oversized for the flow involved in the process.

Another problem with prior art radiation consistency testing systems is the effect of air which becomes mixed into the slurry before testing. Since air attenuates the radiation to a lesser extent than even the water in the solutions, and since water without any intermixed solids is used as a calibration point for testing, the existence of an unknown quantity of air in the slurry, substituting for water within the pipe volume, makes accurate measurement of consistency impossible.

The present invention solves both the problem of extreme pipe diameters and the problem of entrapped air. The present invention eliminates the need for increasing the pipe diameter by configuring the test section so that the radiation path is along the axis of pipe. Thus, the radiation path length can be virtually unlimited even with relatively small flow rates.

This axial path is accomplished by selecting the appropriate length of pipe to furnish the test path desired and locating a pipe elbow at each end of the test pipe. The radiation source is then attached to one pipe elbow so that it is essentially aligned with the axis of the test length of pipe, and the radiation detector is attached to the other pipe elbow, also aligned with the axis of the test length of pipe. The actual test path then includes the test length of pipe and the two legs of two pipe elbows which are aligned with the test length of pipe.

The problem of air affecting the measurement is solved in the present invention by adding a defoaming agent to the slurry before testing. A mixing station is located in the flow path of the testing apparatus so that is precedes the radiation test section. This mixing station simply stirs the slurry as a commercial defoaming agent is added to the slurry. The slurry then flows from the mixing station to the radiation test section, and by the time it is irradiated, it has virtually no air with it.

Calibration of the test system is also quite simple, and requires only the inclusion of a sampling valve near one or the other end of the test path. Since experimentation has shown that the variation in detector signal is essentially linear with changes in slurry consistency, the apparatus need only be calibrated with two different solutions. Moreover, since water alone is the appropriate fluid to give the reading for zero consistency, only one other sample need be taken of a slurry with some other consistency. Calibration points are taken by simply taking a radiation detector reading and simultaneously taking a sample of the slurry from the sampling valve. The sample is then analyzed, giving one point on the consistency calibration slope. The second point on the calibration slope is secured by simply taking a radiation detector reading when only water is flowing through the system.

The only other reading required is a temperature reading, which is secured by the installation of a temperature monitoring device as close to the test pipe section as possible. Since consistency readings vary with temperature, for accuracy it is necessary to verify that the temperature of any slurry flowing through the test section is the same as that for the calibration being used.

With the increased test path length available and air removed from the slurry, the present invention is able to furnish consistency testing results of much higher accuracy than has ever before been available. Now it is a simple matter to attain a six foot long test path with a convenient pipe size of, for example, 1½ inch nominal diameter, while previously a test path of the same length required a pipe, or more likely a vat, with a six foot diameter to attain a comparable accuracy.

The present invention therefore greatly simplifies the installation and operation of consistency testing equipment and furnishes accuracy never before attained and

DETAILED DESCRIPTION OF THE INVENTION

Figure 1:
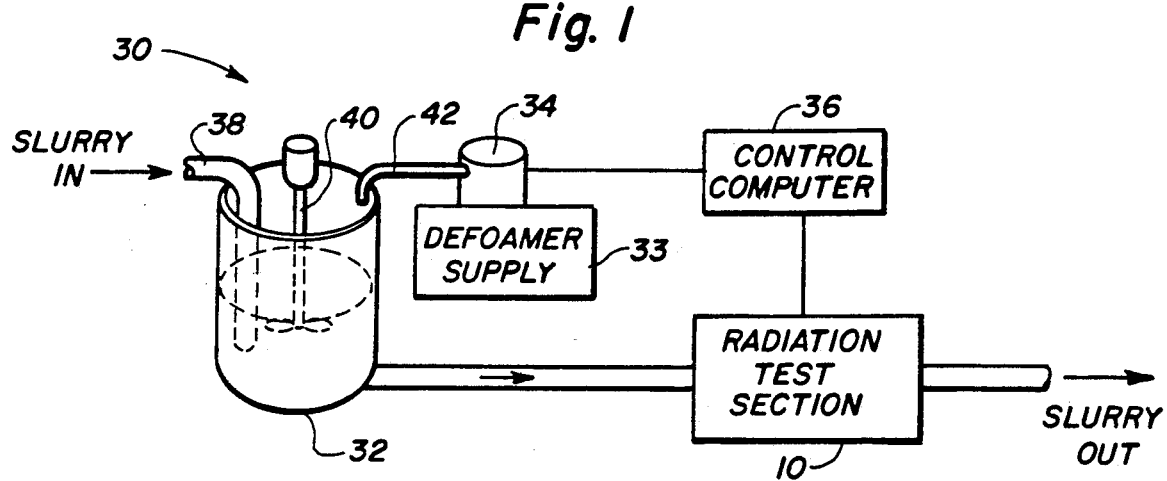
FIG. 1 is a simplified schematic view of the preferred embodiment of the invention.

The preferred embodiment of the invention is shown in FIG. 1 in which consistency tester 30 includes radiation test section 10, deaerating tank 32, defoamer supply system 34, and control computer 36.

Untested slurry is fed to consistency tester 30 at deareating tank 32 from pipe 38. The slurry is generally supplied to deaerating tank 32 below the surface of the slurry already in the tank in order to prevent further entrapment of air. Air within the slurry creates a severe measurement problem because it replaces an unknown quantity of water which is the radiation attenuation standard to which the subsequent radiation test is compared. Normally, the radiation attenuation with only water in the radiation test section is the minimum radiation attenuation achieved, but if air is present in the slurry in any quantity, it counteracts the added attenuation of the solid materials by replacing some volume of water, and the resulting reading is erroneous.

Moreover, regardless of any precautions taken within the test apparatus to prevent air entrapment, the slurry always had some air within it from previous processing. Prior art test apparatus has always merely ignored this problem in hopes that its effect was minor, but it is not. In the present invention, the effect of air in the slurry is completely eliminated by simply eliminating the air itself. This is accomplished by adding a defoaming agent to the slurry while the slurry is in the aerating tank. Defoaming agents, which are available commercially, have the property of separating the air from the liquid and causing the air to rise to the surface of the tank.

In order to assure that all the slurry is subjected to the effect of the defoaming agent, agitator 40 is located within tank 32 to mix the contents of the tank, thereby assuring that the defoaming agent acts upon the slurry and removes the air from it before the slurry is supplied to the radiation test section.

The defoaming agent is added to the slurry in a controller manner by adjustable feed rate pump 34 through pipe 42 which enters tank 32. Pump 34 can be adjusted manually based upon the stability of test results, the quality of resulting product, or the reactions of subsequent processing steps, but it can also be automatically controlled by computer 36 based upon the readings of consistency derived from radiation test section 10.

Figure 2:
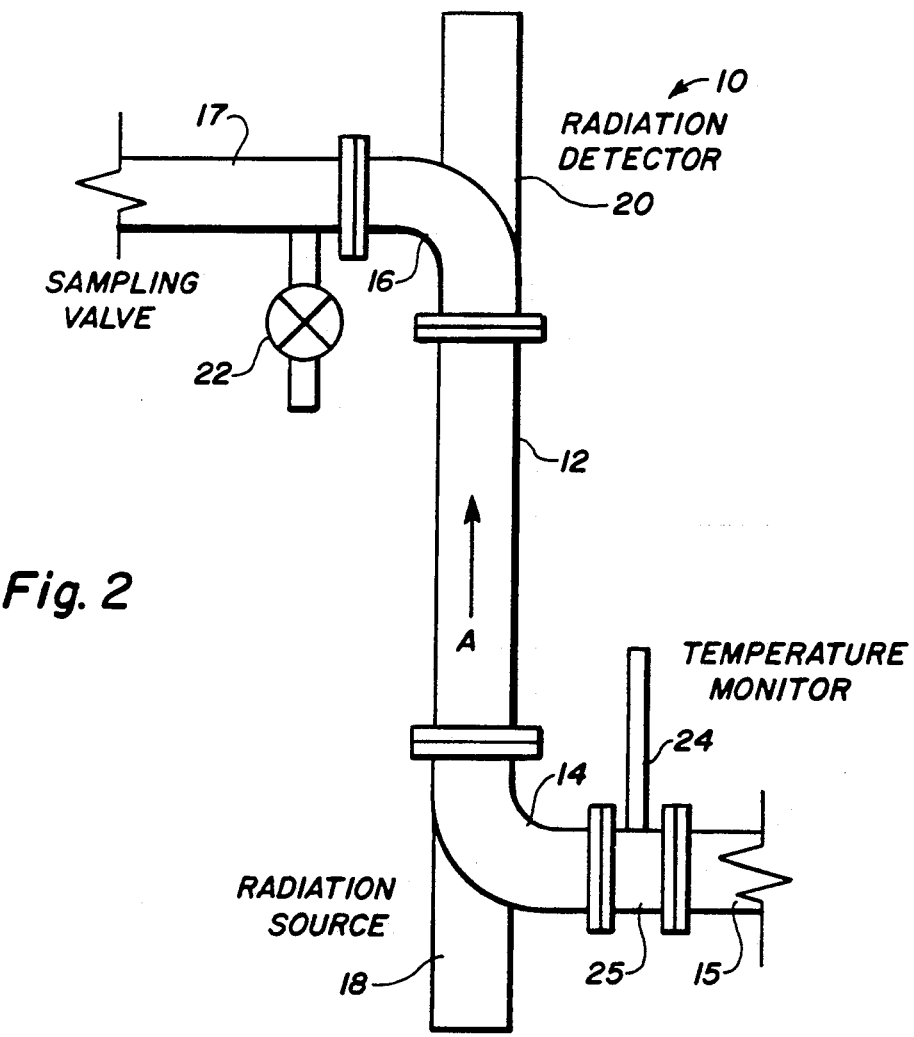
FIG. 2 is a simplified schematic diagram of the radiation test section of the preferred embodiment.

The radiation test section of the invention is shown in FIG. 2 which is a simplified schematic diagram of radiation test section 10 of the invention. FIG. 2 shows the simple configuration of the test section which includes only straight pipe 12, first elbow 14, second elbow 16, radiation source 18, radiation detector 20, sampling valve 22 and temperature monitor 24.

The slurry (not shown) which flows through the piping system into which consistency tester 10 is inserted can actually flow in either direction, but the preferred flow direction A for the vertical pipe configuration as shown in FIG. 2 is best since it assures that straight pipe 12 and elbows 14 and 16 will be filled with slurry. Although FIG. 2 depicts consistency tester 10 with straight pipe 12 oriented vertically, consistency tester 10 could also be located in a horizontal plane if other means were used to assure that straight section 12 and elbows 14 and 16 were filled with slurry during the testing activity.

Straight pipe 12 has attached to at its ends elbow 14 and elbow 16 which themselves are also attached to other sections 15 and 17 respectively of consistency tester 30. In the preferred embodiment, elbow 14 has temperature monitor section 25 attached to it and inserted between it and section 15 so that temperature monitor 24 may be located close to straight section 12 and thereby accurately measure the temperature of slurry within straight section 12.

Sampling valve 22 is also located in a section adjacent to one of the elbows, shown as section 17 in the preferred embodiment, but it can be located anywhere in close proximity to consistency tester 10, including in the same section as temperature monitor 24.

As can be seen in FIG. 2, radiation source 18 and radiation detector 20 are located at and attached to opposite elbows 14 and 16, with straight section 12 between them. Both radiation source 18 and radiation detector 20 are standard available devices in industry, and the radiation detector may be either a scintillation detector or an ionization detector.

Radiation source 18 and radiation detection 20 are aligned so that the radiation path between them is approximately parallel to the axis of straight section 12. Therefore, the radiation path and the length of the test section can be increased to whatever is physically practical so that the total radiation attenuation by the slurry is also increased to a maximum level which permits measurement of smaller changes in consistency.

One alternate embodiment of the invention is to construct consistency tester 10 entirely of pipe which does not attenuate radiation, such as fiberglass. The use of such a pipe eliminates the fixed level of radiation attenuation which would be present with the use of metal pipe, and further increases the ability to distinguish small changes in slurry attenuation, particularly at low consistencies. With metal pipe, the minimum attenuation reading with a water solution also includes the attenuation of the pipe, but with nonattenuating pipe the pipes' added attenuation is eliminated, and the minimum reading truly shows only the effect of the water.

Moreover, fiberglass pipe particularly is less subject to abrasion than is conventional metal pipe. Therefore, another inaccuracy is eliminated which is caused by changed in attenuation as the inside of the metal pipe is worn away by action of the slurry.

The use of radiation test section 10 is particularly simple and is essentially the same as the methods of use with previous consistency testers. A calibration curve is established for any particular type deaerated slurry by taking one reading of the radiation passing through consistency tester 10 and simultaneously taking a sample at sample valve 22. Analysis of the sample established the relationship of slurry consistency to the radiation reading for the temperature at which the radiation reading was taken. A radiation reading with only deaerated water in the system furnishes the only other calibration point required to establish a calibration slope, since the calibration relationship is linear. Later reading of consistency need only assure there is no air in the slurry and then refer to this established calibration slop and adjust for temperature for any radiation reading to secure highly accurate consistency measurements. Of course, this calibration and reading procedure can easily be computerized so that it is completely automatic.

The present invention therefore furnishes a much more precise slurry consistency tester than has previously been available, because it effectively expands the scale with which radiation attenuation readings can be taken and eliminates errors from air present in the test slurry.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims. For instance, elbows 14 and 16 could be oriented with their legs parallel and attached to a storage tank, as long as the storage tank is filled enough to fill consistency tester 10 with slurry.

What is claimed is:

1. An apparatus for testing the consistency of slurry solutions comprising:
   (a) a deaerating means which receives a slurry to be tested and removes entrapped gases from the slurry;
   (b) a radiation test section interconnected with the deaerating means, receiving slurry from the deaerating means and providing a measurement of the consistency of the slurry by measuring the attenuation of radiation which occurs when radiation is passed through a prescribed path through a portion of the slurry;
   (c) the radiation test section comprises:
      (1) a straight section of pipe with the total amount of slurry flowing therethrough;
      (2) a first pipe elbow attached to one end of the straight section of pipe;
      (3) a radiation source attached to the first pipe elbow so that the radiation from the radiation source is essentially aligned with the axis of the straight section of pipe;
      (4) a second pipe elbow attached to the second end of the straight section of pipe; and
      (5) a radiation detector attached to the second pipe elbow so that the radiation detector is affected by the radiation from the radiation source, and the radiation received by the radiation detector is affected by the consistency of the slurry as measured in the total flow of the slurry and not a sample of the slurry;
   (d) the deaerating means comprimises:
      (1) a container into which the slurry is fed;
      (2) supply means to furnish a controlled quantity of defoaming agent into the container; and
      (3) mixing means which assures that the defoaming agent acts upon the slurry before the slurry is supplied to the radiation test section; and
   (e) including control means interconnected with the radiation test section and the supply means and acting to determine the rate of supply of defoaming agent to the deaerating means based upon the consistency reading derived from the radiation test section.

2. The apparatus of claim 1 further including a means to remove a sample of the slurry from a location near the radiation test section.

3. The apparatus of claim 1 further including a means to measure the temperature of the slurry within the radiation test section.

* * * * *